US006242577B1

(12) United States Patent
Ruoslahti et al.

(10) Patent No.: US 6,242,577 B1
(45) Date of Patent: Jun. 5, 2001

(54) ISOLATION AND USE FIBRONECTIN RECEPTOR

(75) Inventors: Eric I. Ruoslahti, Rancho Santa Fe; Michael D. Pierschbacher, San Diego, both of CA (US)

(73) Assignee: La Jolla Cancer Research Foundation, La Jolla, CA (US)

( * ) Notice: Subject to any disclaimer, the term of this patent is extended or adjusted under 35 U.S.C. 154(b) by 0 days.

(21) Appl. No.: 09/082,229

(22) Filed: May 20, 1998

Related U.S. Application Data

(62) Division of application No. 08/468,480, filed on Jun. 5, 1995, now Pat. No. 5,766,857, which is a division of application No. 08/056,815, filed on Apr. 29, 1993, now Pat. No. 5,540,933, which is a continuation of application No. 07/857,097, filed on Mar. 20, 1992, now abandoned, which is a continuation of application No. 07/302,047, filed on Jan. 25, 1989, now abandoned, which is a continuation of application No. 06/740,240, filed on May 31, 1985, now abandoned.

(51) Int. Cl.$^7$ .................................................. C07K 16/28

(52) U.S. Cl. ................................. 530/388.22; 530/389.1

(58) Field of Search ............................ 530/388.22, 389.1

(56) References Cited

U.S. PATENT DOCUMENTS

| | | |
|---|---|---|
| 4,483,928 | 11/1984 | Suzuta et al. . |
| 4,565,789 | 1/1986 | Liotta et al. . |
| 4,578,079 | 3/1986 | Ruoslahti et al. . |
| 4,589,881 | 5/1986 | Pierschbacher et al. . |
| 4,879,237 | 11/1989 | Ruoslahti .............................. 435/375 |

OTHER PUBLICATIONS

Pierschbacher, MD, Hayman, EG, and Ruoslahti, E. Location of the cell–attachment site in fibronectin with monoclonal antibodies and proteolytic fragments of the molecule. Cell, 26:259–267, Oct. 1981.
Oesch, B and Birchmeier, W. New surface component of fibroblast's focal contacts identified by a monoclonal antibody. Cell, 31:671–679 (Part 2), Dec. 1982.
Hynes et al., *Cell*48:549–554 (1987).
Takada et al., *Nature*, 326:607–609 (1987).
Horwitz et al., *Nature*, 320:531–533 (1986).
Gardner et al., "Interaction of Fibronectin with its Receptor on Platelets," *Cell*42:439–448 (1985).
Pierschbacher, *Proc. Natl. Acad. Sci. USA*, 80:1224–1227 (1983).
Brown, "Selective Inhibition of Fibronectin–Mediated Cell Adhesion by Monoclonal Antibodies to a Cell–Surface Glycoprotein," *Science*228:1448–1451 (1985).
Pytela et al., "Identification and Isolation of a 140 kD Cell Surface Glycoprotein with Properties Expected of a Fibronecting Receptor," *Cell* 40:191–198 (1985).

Lehto et al., "Enrichment of a 140 kD Surface Glycoprotein in adherent, Detergent–Resistant Cytoskeleton of Cultured Human Fibroblasts," *Biochemical and Biophysical Research Come.*, 95(3):909–906(1980).
Greve et al., "Monoclonal Antibodies Which Alter the Morphology of Cultured Chick Myogenic Cells," *J. Cell Biochem.*, 18:222–229 (1982).
Horwitz et al., "The Cell Substrate Attachment (SAT) Antigen has Properties of a Receptor For Laminin and Fibronecting," *J. Cell Biol*, 101:2134–2144 (1985).
Neff et al., "A Monoclonal Antibody Detaches Embryonic Skeletal Muscle From Extracellular Matrices," *J. Cell Biol.*, 95:654–666 (1982).
Horwitz et al., "Interaction of Plasma Membrane Fibronectin Receptor with Talin–A Transmembrane Linkage," *Nature*, 320:531–533 (1986).
Pierschbacher et al., "Variants of the Cell Recognition Site of Fibronectin That Retain Attachment–Promoting Activity," *Proc. Natl. Acad. Sci. USA*, 81:5985–5988 (1984).
Pierschbacher et al., "Cell Attachment Activity of Fibronectin Can Be Duplicated by Small Synthetic Fragments of the Molecule," *Nature*, 309 (5963) : 30–33 (1984).
Plow et al., "The Effect of ARG–GLY–ASP–Containing Peptides on Fibronectin and Vol Willebrand Factor Binding to Platelets," *Proc. Natl. Acad. Sci. USA*, 82:8057–8061 (1985).
Pytela et al., "Platelet Membrane Glycoprotein IIb/IIa: Member of a Family of ARG–GLY–ASP–Specific Adhesion Receptors," *Science* 23:1559–1562 (1986).
Ginsberg et al., "Inhibition of Fibronectin Binding to Platelets by Proteolytic Fragments and Synthetic Peptides Which Support Fibroblast Adhesion," *J. Biol. Chem.*, 260:(7):3931–3936 (1985).
Haverstick et al., "Inhibition of Platelet Adhesion of Fibronectin, Fibronectin, and Von Willebrand Factor Substrates by a Synthetic Tetrapeptide Derived From the Cell–Binding Domain of Fibronectin," *Blood*66: (4):946–952 (1985).
Gartner et al., "The Tetrapeptide Analogue of the Cell Attachment Site of Fibronectin Inhibits Platelet Aggregation and Fibrinogen Binding to Activated Platelets," *J. Biol. Chem.*, 260: (22) : 11891–11894 (1985).
ILL et al., "Adhesion of Platelets to Laminin in the Absence of Activation," *J. Cell Biol.*, 99:2140–2145(1984).
Pierschbacher et al., "Synthetic Peptide with Cell Attachment Activity of Fibronectin," *Proc. Natl. Acad. Sci. USA*, J. Cell. Biochem., 80:1224–1227 (1983).

(List continued on next page.)

Primary Examiner—David Saunders
Assistant Examiner—Mary Beth Tung
(74) *Attorney, Agent, or Firm*—Campbell & Flores LLP

(57) ABSTRACT

Method for the isolation and characterization of a 140,000 dalton cell surface glycoprotein with the properties expected of a fibronectin receptor is described.

1 Claim, 8 Drawing Sheets

OTHER PUBLICATIONS

Giancotti et al., "Elevated Levels of the $\alpha_5\beta_1$ Fibronectin Receptor Suppress the Transformed Phenotype of Chinese Hamster Ovary Cells," *Cell* 60:849–858 (1990).

Damsky et al., *J. Cell Biol.*, 100:1528–1539 (1985).

Freifelder, *Physical Biochemistry*, 2d Ed., New York:Freeman and Co., 333–338, 346–353 (1982).

Brown et al., *J. Cell Biol.*, 99:161a Abstract 593 (1984).

Chen et al., "Development of Cell Surface Linkage Complexes in Cultured Fibroblasts," *J. Cell. Biol.*, 100:1103–1114 (1985).

Ruoslahti, Erkki, "Fibronectin and Its Receptors," *Ann. Rev. Biochem.* 57:375–413 (1988).

Tamkum et al., "Structure of Integrin, A Glycoprotein Involved in the Transmembrane Linkage Between Fibronectin and Actin," *Cell.*, 46:271–282 (1986).

ISOLATION AND USE FIBRONECTIN RECEPTOR

This application is a divisional of application Ser. No. 08/468,480, filed Jun. 5, 1995, now U.S. Pat. No. 5,766,857, which is a divisional of application Ser. No. 08/056,815, filed Apr. 29, 1993, now U.S. Pat. No. 5,540,933 which is a continuation of application Ser. No. 07/857,097, filed Mar. 20, 1992, abandoned, which is a continuation of application Ser. No. 07/302,047, filed Jan. 25, 1989, abandoned, which is a continuation of application Ser. No. 06/740,240, filed May 31, 1985, abandoned.

FIELD OF THE INVENTION

This invention relates generally to the field of biochemistry and more particularly to a cell surface glycoprotein having the apparent molecular weight of 140,000 daltons with the properties expected of a fibronectin receptor, and the use of the receptor to prepare liposomes with predetermined adhesion properties.

BACKGROUND OF THE INVENTION

Cell-substrate adhesion is generally considered to be a multistep process involving recognition of extracellular matrix components by cell surface receptors, followed by cytoskeletal rearrangements that lead to cell spreading (Grinnell, 1978; Hynes, 1981). Several extracellular matrix glycoproteins, such as fibronectin (Ruoslahti, et al., 1981b), laminin (Timpl, et al., 1979), vitronectin (Hayman, et al., 1983), and collagens have been shown to promote attachment of various cell types to tissue culture substrates (Kleinman, et al., 1981). The cell membrane receptors that recognize these matrix proteins, however, remain essentially unknown, although putative receptors for laminin (Lesot, et al., 1983; Malinoff and Wicha, 1983) and collagens (Chiang and Kang, 1982; Mollenhauer and von der Mark, 1983) are currently being investigated.

A number of candidates for the role of a fibronectin receptor have been proposed. By photoaffinity labeling, it was shown that a 49 kd glycoprotein comes into close contact with substrate-bound fibronectin (Aplin, et al., 1981). Further support for the notion that the receptor is a protein comes from studies showing that treatment of cells with certain proteases abolishes the ability of cells to attach to fibronectin (Tarone, et al., 1982). Treatment with trypsin, however, at least in the presence of $Ca^{++}$, leaves the receptor activity intact (Oppenheimer-Marks and Grinnell, 1984). Based upon the calcium-dependent stability to trypsin, Oppenheimer-Marks and Grinnell (1984) have proposed a 48 kd wheat germ agglutinin-binding glycoprotein as a potential fibronectin receptor.

It has also been suggested that heparan sulfate proteoglycans might be involved in cell attachment to fibronectin (Culp, et al., 1979; Laterra, et al., 1983). Indeed, photocross-linking experiments performed by Perkins, et al. (1979) showed that proteoglycans are associated with fibronectin at the cell surface.

A different type of cell surface component has been implicated in fibronectin-cell interactions by studies showing an inhibitory effect of di- and trisialogangliosides on the attachment of cells to fibronectin (Kleinman, et al., 1979). The inhibitory activity was found to reside in the carbohydrate moiety of the glycolipid. Antibodies that interfere with cell attachment have been described by a number of investigators, and the corresponding antigens have been found to be proteins with molecular weights ranging from 60 to 160 kd (Hsieh and Sueoka, 1980; Knudsen, et al., 1981; Neff, et al., 1982; Greve and Gottlieb, 1982; Oesch and Birchmeier, 1982), or specific gangliosides (Dippold, et al., 1984).

A large number of binding affinities are known to be present in the fibronectin molecule, such as for collagen (Engvall and Ruoslahti, 1977), fibrinogen and fibrin (Ruoslahti and Vaheri, 1975), proteoglycans (Stathakis and Mosesson, 1977), cell surfaces (Klebe, 1974; Pearlstein, 1976), and actin (Keski-Oja, et al., 1980), and there have been some studies of the interaction of cell surfaces with the cell attachment site. (Pierschbacher, et al., 1981). A large fibronectin fragment, that promotes cell attachment but lacks the other binding activities is also known, (Pierschbacher, et al., 1982, 1983; Pierschbacher and Ruoslahti, 1984a).

It has now been discovered that a 140 kd protein from detergent extracts of cells, when incorporated into liposomes, promotes their binding specifically to fibronectin-coated substrates via the Arg-Gly-Asp sequence in the fibronectin molecule.

REFERENCES

The content of the following references is incorporated into the foregoing specification, as fully as though set forth therein as a background for those skilled in the art.

Aplin, J. D., Hughes, R. C., Jaffe, C. L., and Sharon, N. (1981) Reversible cross-linking of cellular components of adherent fibroblasts to fibronectin and lectin-coated substrata. Exp. Cell Res. 134, 488–494.

Billiau, A., Edy, V. G., Heremans, H., Van Damme, J., Desmyter, J., Georgiades, J. A., and DeSomer, P. (1977). Human interferon: mass production in a newly established cell line, MG-63. Antimicrob. Agents Chemother. 12, 11–15.

Cheresh, D. A., Harper, J. R., Schulz, G., and Reisfeld, R. A. (1984). Localization of the gangliosides $GD_2$ and $GD_3$ in adhesion plaques and on the surface of human melanoma cells. Proc. Nat. Acad. Sci. USA 81, in press.

Chiang, T. M., and Kang, A. H. (1982). Isolation and purification of collagen αl(I) receptor from human platelet membrane. J. Biol.Chem. 257, 7581–7586.

Culp. L. A., Murray, B. A., and Rollins, B. J. (1979). Fibronectin and proteoglycans as determinants of cell-substratum adhesion. J. Supramol. Struct. 11, 401–427.

Dippold, W. G., Knuth, A., and Meyer zum Büschenfelde, K. (1984). Inhibition of human melanoma cell growth in vitro by monoclonal anti-GD3-ganglioside antibody. Cancer Res. 44, 806–810.

Engvall, E., and Ruoslahti, E. (1977). Binding of soluble form of fibroblast surface protein, fibronectin, to collagen. Int. J. Cancer 20, 1–5.

Engvall, E., Krusius, T., Wewer, U., and Ruoslahti, E. (1983). Laminin from rat yolk sac tumor: isolation, partial characterization, and comparison with mouse laminin. Arch. Biochem. Biophys. 222, 649–656.

Greve, J. M., and Gottieb, D. I. (1982). Monoclonal antibodies which alter the morphology of cultured chick myogenic cells. J. Cell. Biochem. 18, 221–229.

Grinnell, F. (1978). Cellular adhesiveness and extracellular substrata. Int. Rev. Cyto. 53, 65–144.

Hayman, E. G., Engvall, E., and Ruoslahti, E. (1981). Concomitant loss of cell surface fibronectin and laminin from transformed rat kidney cells. J. Cell Biol. 88, 352–357.

Hayman, E. G., Pierschbacher, M. D., Ohgren, Y., and Ruoslahti, E. (1983). Serum spreading factor (vitronectin) is present at the cell surface and in tissues. Proc. Nat. Acad. Sci. USA 80, 4003–4007.

Hoffman, S., Sorkin, B. C., White, P. C., Brackenbury, R., Mailhammer, R., Rutishauser, U., Cunningham, B. A., and Edelman, G. M. (1982). Chemical characterization of a neural cell adhesion molecule purified from embryonic brain membranes. J. Biol. Chem. 257, 7720–7729.

Hsieh, P., and Sueoka, N. (1980). Antisera inhibiting mammalian cell spreading and possible cell surface antigens involved. J. Cell Biol. 86, 866–873.

Hynes, R. O. (1981). Relationships between fibronectin and the cytoskeleton. In Cell Surface Reviews, Vol. 7, G. Poste and G. L. Nicolson, eds (Amsterdam: Elsevier/North Holland), pp. 97–136.

Keski-Oja, J., Sen. A., and Todaro, G. S. (1980). Direct association of fibronectin and actin molecules in vitro. J. Cell Biol. 85, 527.

Klebe, R. J. (1974). Isolation of a collagen-dependent cell attachment factor. Nature 250, 248–251.

Kleinman, H. K., Martin., G. R., and Fishman, P. H. (1979). Ganglioside inhibition of fibronectin mediated cell adhesion to collagen. Proc. Nat. Acad. Sci. USA 76, 3367–3371.

Kleinman, H. K., Klebe, R. J., and Martin, G. R. (1981). Role of collagenous matrices in the adhesion and growth of cells. J. Cell Biol. 88, 473–485.

Knudsen, K. A., Rao, P. E., Damsky, C. H., and Buck, C. A. (1981). Membrane glycoproteins involved in cell-substratum adhesion. Proc. Nat. Acad. Sci. USA 78, 6071–6075.

Laemmli, U. K. (1970). Cleavage of structural proteins during the assembly of the head of bacteriophage T4. Nature 227, 680–685.

Laterra, J., Siebert, J. E., and Culp, L. A. (1983). Cell surface heparan sulfate mediates some adhesive responses to glycosaminoglycan-binding matrices, including fibronectin. J. Cell Biol. 96, 112–123.

Lebien, T. W., Boue, D. R., Bradley, J. G., and Kersey, J. H. (1982). Antibody affinity may influence antigenic modulation of the common acute lymphoblastic leukemia antigen in vitro. J. Immunol. 129, 2287–2292.

Lesot, H., Kühl, U., and von der Mark, K. (1983) Isolation of a laminin-binding protein from muscle cell membranes. EMBO J. 2, 861–865.

Malinoff, H. L., and Wicha, M. S. (1983). Isolation of a cell surface receptor protein for laminin from murine fibrosarcoma cells. J.Cell Biol. 96, 1475–1479.

McAbee, D. D., and Grinnell, F. (1983). Fibronectin-mediated binding and phagocytosis of polystyrene latex beads by baby hamster kidney cells. J. Cell Biol. 97, 1515–1523.

McKeown-Longo, P. J., and Mosher, D. F. (1983). Binding of plasma fibronectin to cell layers of human skin fibroblasts. J. Cell Biol. 97, 466–472.

Mimms, L. T., Zampighi, G., Nozaki, Y., Tanford, C., and Reynolds, J. A. (1981). Phospholipid vesicle formation and transmembrane protein incorporation using octyl glucoside. Biochemistry 20, 833–840.

Mollenhauer, J., and von der Mark, K. (1983). Isolation and characterization of a collagen-binding glycoprotein from chondrocyte membranes. EMBO J. 2, 45–50.

Neff, N. T., Lowrey, C., Decker, C., Tovar, A., Damsky, C., Buck, C., and Horwitz, A. F. (1982). A monoclonal antibody detaches embryonic skeletal muscle from extracellular matrices. J. Cell Biol. 95, 654–666.

Oesch, B., and Birchmeier, W. (1982). New surface component of fibroblast's focal contacts identified by a monoclonal antibody. Cell 31, 671–679.

Oppenheimer-Marks, N., and Grinnell, F. (1982). Inhibition of fibronectin receptor function by antibodies against baby hamster kidney cell wheat germ agglutinin receptors. J. Cell Biol. 95, 876–884.

Oppenheimer-Marks, N., and Grinnell, F. (1984). Calcium ions protect cell-substratum adhesion receptors against proteolysis. Exp. Cell Res. 152, 467–475.

Pearlstein, E. (1976). Plasma membrane glycoprotein which mediates adhesion of fibroblasts to collagen. Nature 262, 497–500.

Perkins, M. E., Ji, T. H., and Hynes, R. O. (1979). Cross-linking of fibronectin to sulfated proteoglycans at the cell surface. Cell 16, 941–952.

Pierschbacher, M. D., and Ruoslahti, E. (1984a). Cell attachment activity of fibronectin can be duplicated by small synthetic fragments of the molecule. Nature 309, 30–33.

Pierschbacher, M. D., and Ruoslahti, E. (1984b). Variants of the cell recognition site of fibronectin that retain attachment-promoting activity. Proc. Nat. Acad. Sci. USA 81, 5985–5988.

Pierschbacher, M. D., Hayman, E. G. and Ruoslahti, E. (1981). Location of the cell attachment site in fibronectin with monoclonal antibodies and proteolytic fragments of the molecule. Cell 26, 259–267.

Pierschbacher, M. D., Ruoslahti, E., Sundelin, J., Lind, P., and Peterson, P. A. (1982). The cell attachment domain of fibronectin. Determination of the primary structure. J. Biol. Chem. 267, 9593–9597.

Pierschbacher, M. D., Hayman, E. G., and Ruoslahti, E. (1983) Synthetic peptide with cell attachment activity of fibronectin. Proc. Nat. Acad. Sci. USA 80, 1224–1227.

Rauvala, H., Carter, W. G., and Hakomori, S.-I. (1981). Studies on cell adhesion and recogition I. Extent and specificity of cell adhesion triggered by carbohydrate-reactive proteins (glycosidases and lectins) and by fibronectin. J. Cell Biol. 88, 127–137.

Ruoslahti, E., and Vaheri, A. (1975). Interaction of soluble fibroblast surface antigen with fibrinogen and fibrin. J. Exp. Med. 141, 497–501.

Ruoslahti, E., Hayman, E. G., Engvall, E., Cothran, W. C., and Butler, W. T. (1981a). Alignment of biologically active domains in the fibronectin molecule. J. Biol. Chem. 256, 7277–7281.

Ruoslahti, E., Engvall, E., and Hayman, E. G. (1981b). Fibronectin: current concepts of its structure and function. Coll. Rel. Res. 1, 95–128.

Stathakis, N. E., and Mosesson, M. W. (1977). Interactions among heparin, cold-insoluble globulin, and fibronectin in formation of the heparin-precipitable fraction of plasma. J. Clin. Invest. 60, 855–865.

Tarone, G., Galetto, G., Prat, M., and Comoglio, P. M. (1982). Cell surface molecules and fibronectin-mediated cell adhesion: effect of proteolytic digestion of membrane proteins. J. Cell Biol. 94,179–186.

Timpl, R., Rohde, H., Robey, P. G., Rennard, S. I., Foidart, J. M., and Martin, G. R. (1979). Laminin-a glycoprotein from basement membranes. J. Biol. Chem. 254, 9933–9937.

Yoshida, C., and Takeichi, M. (1982). Teratocarcinoma cell adhesion: identification of a cell-surface protein involved in calcium-dependent cell aggregation. Cell 28, 217–224.

SUMMARY OF THE INVENTION

The present invention relates to the discovery, identification, separation and isolation, and the use of a cell surface glycoprotein characterized in that it has a molecular weight of about 140,000 daltons, interacts with the cell attachment site in fibronectin and is substantially separated from interfering and diluting cell surface glycoproteins.

As a composition of matter, the invention may be described as consisting essentially of cell surface glycoprotein characterized in that it has a molecular weight of about 140,000 daltons, interacts with the cell attachment site in fibronectin, is eluted from such cell attachment site by a peptide consisting essentially of the amino acid sequence Arginine, Glycine, Aspartic Acid (ARG-GLY-ASP), and is substantially separated from interfering cell surface glycoproteins.

The composition may also be described as consisting essentially of cell surface glycoprotein characterized in that it has a molecular weight of about 140,000 daltons, interacts with the cell attachment site in fibronectin, can be labelled by a procedure which is specific for cell surface proteins, and is substantially separated from interfering cell surface glycoproteins.

The invention, in one facet, may be described as a cell surface glycoprotein characterized in that it has a molecular weight of about 140,000 daltons, interacts with the cell attachment site in fibronectin, incorporates into lipid vesicles, and is substantially separated from interfering cell surface glycoproteins.

The invention also contemplates a method utilizing a composition for targeting liposomes to fibronectin-containing tissues consisting essentially of a cell surface glycoprotein having a molecular weight of about 140,000 daltons which interacts with the cell attachment site in fibronectin and is eluted from such cell attachment site by a peptide consisting essentially of the sequence ARG-GLY-ASP.

The composition for targeting liposomes to fibronectin containing tissues may, in a preferred form, consist essentially of cell surface glycoprotein having a molecular weight of about 140,000 daltons which interacts with the cell attachment site in fibronectin, is eluted from such cell attachment site by a peptide consisting essentially of the sequence ARG-GLY-ASP.

The invention, in another feature, is a method of targeting liposomes to fibronectin containing tissues comprising exposing such tissues to liposomes containing cell surface glycoprotein characterized in that it has a molecular weight of about 140,000 daltons, interacts with the cell attachment site in fibronectin and is substantially separated from interfering and diluting cell surface glycoproteins.

The preferred method of targeting liposomes to fibronectin containing tissues comprises exposing such tissues to liposomes containing a cell surface glycoprotein characterized in that it has a molecular weight of about 140,000 daltons, interacts with the cell attachment site in fibronectin, is eluted from such cell attachment site by a peptide consisting essentially of the sequence ARG-GLY-ASP, and is substantially separated from interfering cell surface glycoproteins.

The method of targeting liposomes to fibronectin containing tissues may comprise exposing such tissues to liposomes containing a cell surface glycoprotein having a molecular weight of about 140,000 daltons which interacts with the cell attachment site in fibronectin, is eluted from such cell attachment site by a peptide consisting essentially of the sequence ARG-GLY-ASP, labelled by a procedure which is specific for cell surface proteins.

As a new composition of matter suitable for assay and detection purposes, the invention is at least one liposome containing a cell surface glycoprotein characterized in that it has a molecular weight of about 140,000 daltons, interacts with the cell attachment site in fibronectin, is eluted from such cell attachment site by a peptide consisting essentially of the sequence ARG-GLY-ASP, and is substantially separated from interfering cell surface glycoproteins.

The liposome composition preferably contains labelled cell surface glycoprotein having a molecular weight of about 140,000 daltons which interacts with the cell attachment site in fibronectin and is eluted from such cell attachment site by a peptide consisting essentially of the sequence ARG-GLY-ASP.

As assay reagent, the invention may be described as consisting essentially of a carrier and cell surface glycoprotein characterized in that it has a molecular weight of about 140,000 daltons, interacts with the cell attachment site in fibronectin, incorporates into lipid vesicles, and is substantially separated from interfering cell surface glycoproteins.

The assay reagent preferably consists essentially of a carrier and a labelled cell surface glycoprotein having a molecular weight of about 140,000 daltons which interacts with the cell attachment site in fibronectin, is eluted from such cell attachment site by a peptide consisting essentially of the sequence ARG-GLY-ASP.

The assay reagent may also consist essentially of a carrier and at least one liposome containing cell surface glycoprotein characterized in that it has a molecular weight of about 140,000 daltons, interacts with the cell attachment site in fibronectin, incorporates into lipid vesicles, and is substantially separated from interfering cell surface glycoproteins. The assay reagent preferably includes cell surface glycoprotein having a molecular weight of about 140,000 daltons which interacts with the cell attachment site in fibronectin and is eluted from such cell attachment site by a peptide consisting essentially of the sequence ARG-GLY-ASP. The cell-cell surface glycoprotein can be labelled by a procedure which is specific for cell surface proteins.

The compositions and methods of this invention are not limited to the specific examples given herein; rather, these compositions and methods are fundamental tools and will find broad applicability in scientific research, clinical assays and therapy.

DETAILED DESCRIPTION OF THE INVENTION

Extracts of surface-labeled cells were fractionated on an immobilized fibronectin fragment that is capable of promoting cell attachment. Human osteosarcoma MG-63 cells that had first been surface-iodinated with lactoperoxidase were dissolved in octylglucoside. MG-63 cells attach to and spread on fibronectin, and deposit fibronectin-containing extracellular matrix fibers in a manner similar to that of normal fibroblast cell lines.

An affinity matrix was prepared by coupling to Cyanogen-Bromide (CNBr)-activated SEPHAROSE a 120 kd chymotryptic fragment of fibronectin that binds to neither gelatin nor heparin but retains cell-attachment-promoting activity (Ruoslahti, et al., 1981a; Pierschbacher, et al., 1981). Specific elution was effected by treating the column with the synthetic peptide:

glycyl-L-arginyl-glycyl-L-aspartyl-L-seryl-L-proline (GRGDSP), which contains the cell-attachment recognition site of fibronectin (Pierschbacher and Ruoslahti, 1984a, 1984b). The eluted fractions were analyzed by SDS-PAGE followed by silver staining and autoradiography for detection of total protein and radioactively labeled surface proteins, respectively.

Figure 1A:
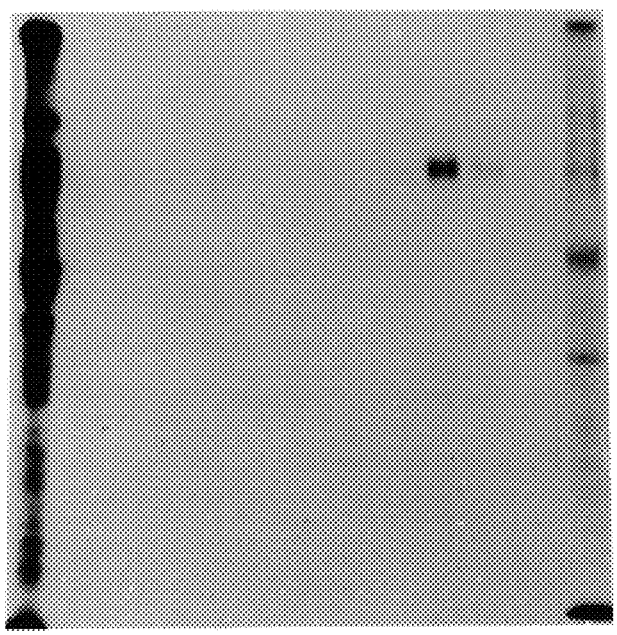
FIG. 1 is a representation of sodium dodecyl sulfate-polyacrylamide gel electrophoresis (SDS-PAGE) analysis of fractions eluted from the fibronectin cell-binding fragment affinity matrix. MG-63 human osteosarcoma cells ($10^8$ cells) were surface-labeled and extracted as described in Example I. The extract (2 ml) was chromatographed on a column of Sepharose 4B (bed volume 2 ml) containing a covalently bound, cell-attachment-promoting fragment of fibronectin. Fractions of 1 ml were collected, and aliquots (50 $\mu$l) of each fraction were analyzed by SDS-PAGE (7.5% acrylamide) under reducing conditions, using autoradiography (A) or silver staining (B) for visualization of protein bands. Where indicated by arrows, 1 mg/ml of the synthetic peptide glycyl-L-arginyl-glycyl-L-glutamyl-L-seryl-L-proline (GRGESP) or glycyl-L-arginyl-glycyl-L-aspartyl-L-seryl-L-proline (GRGDSP) was added to the elution buffer. Lane 1, flow-through; lanes 2–12, column fractions obtained by washing the starting buffer alone or supplemented with peptides; lane 13, material eluted with 8 M urea. Arrowheads denote the position of the 140 kd protein. Molecular weight markers in this and subsequent figures were: myosin, 200 kd; β-galactosidase, 116 kd; phosphorylase B, 94 kd; bovine serum albumin, 67 kd; ovalbumin, 43 kd.

As shown in FIG. 1A, a radioactive protein with an apparent molecular weight of 140 kd specifically eluted from the affinity matrix with the GRGDSP peptide (lanes 9–12). The affinity of the 140 kd protein for the matrix was essentially unaffected by a related peptide (lanes 4–7) in which the aspartic acid residue is replaced by glutamic acid (GRGESP). Since this peptide does not promote cell attachment (Pierschbacher and Ruoslahti, 1984b), but does have structural and charge propertites closely similar to those of the active peptide, the resistance of the 140 kd protein toward elution with this peptide establishes the specificity of the elution with the active peptide. No specific protein bands could be obtained by the same elution procedure when albumin-SEPHAROSE was used instead of the fibronectin fragment-SEPHAROSE.

Figure 1B:
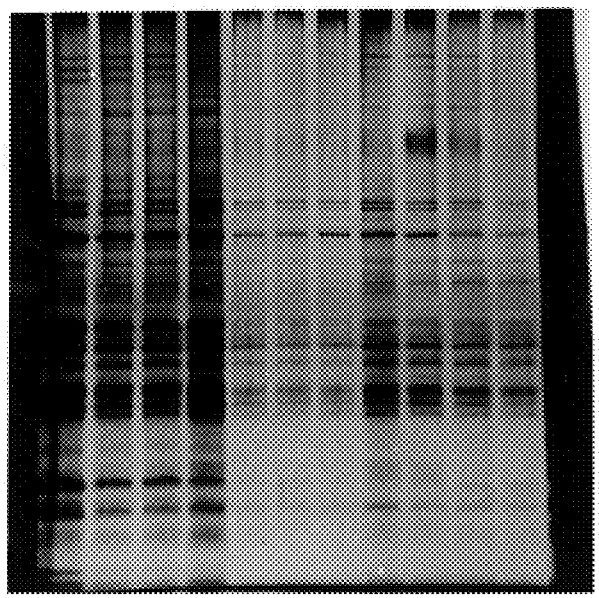

Silver-stained SDS-PAGE (FIG. 1B) showed that the 140 kd protein was a major component among the proteins eluted from the fibronectin fragment column. It appeared as a darkly stained, diffuse band. The silver staining also revealed the presence of a number of other protein bands in the eluted material. The elution of these additional bands, however, was not dependent upon the GRGDSP peptide, and they were not labeled by lactoperoxidase-catalyzed iodination of intact cells. Thus, it appears that these bands represent intracellular, possibly cytoskeletal, proteins that bind nonspecifically to the column and slowly leach off during the elution.

Elution of the affinity column with urea subsequent to the elution with the GRGDSP peptide resulted in the release of a large number of proteins (FIG. 1, lanes 13). This underlines the high specificity provided by the elution with the synthetic cell-attachment peptide. The urea eluate did not contain detectable amounts of the 140 kd protein, suggesting that it had been quantitatively removed from the column by elution with the GRGDSP peptide.

Figure 2:
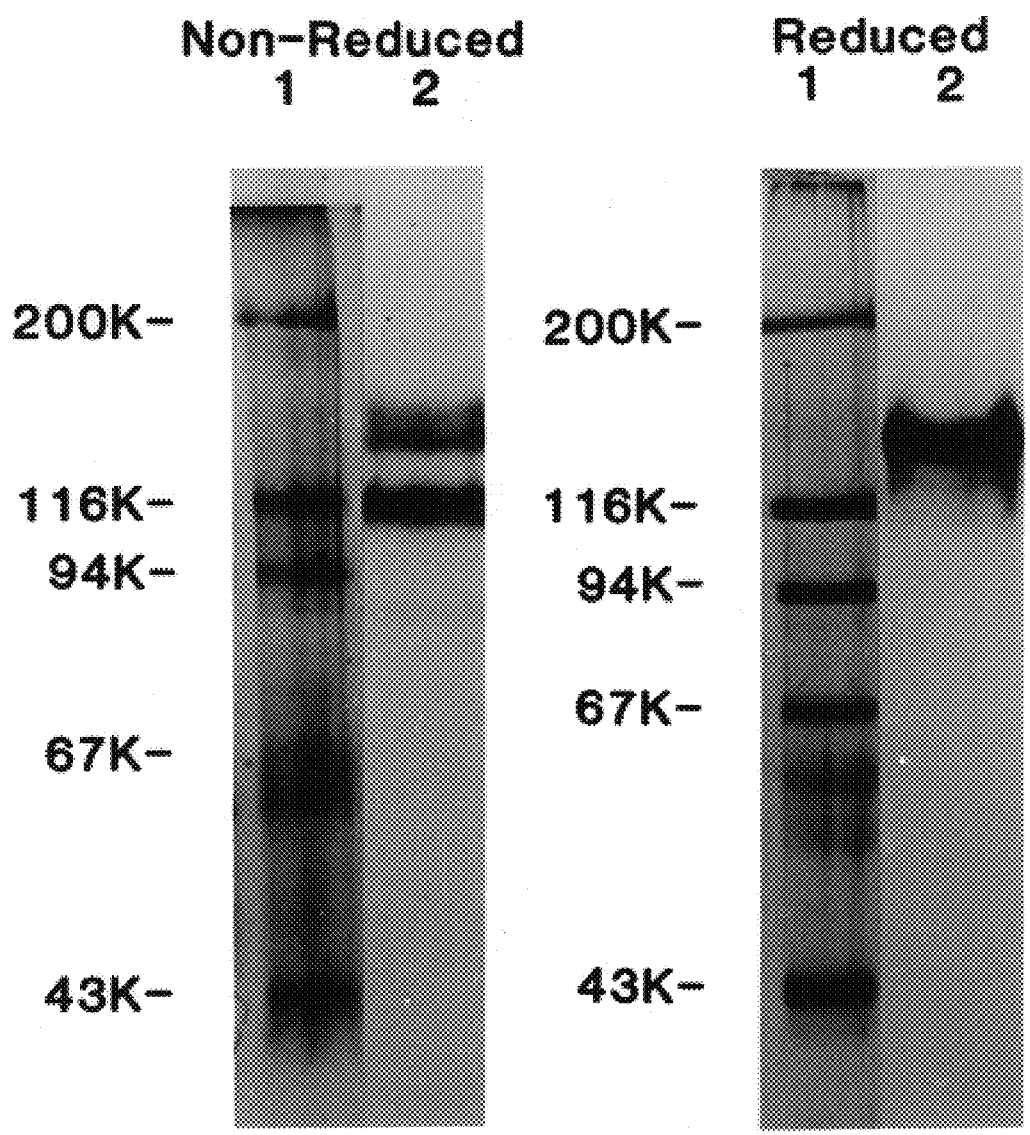
FIG. 2 is a representation of the analysis of the 140 kd protein by SDS-PAGE under nonreducing conditions. A preparation of radiolabeled 140 kd protein, as shown in FIG. 1, lane 10, and molecular weight markers were subjected to SDS-PAGE under nonreducing and reducing conditions. The nonreduced and reduced samples were run on separate gels. Lane 1, molecular weight markers visualized using silver staining; lane 2, 140 kd protein visualized using autoradiography.

When the $^{125}$I-labeled, affinity-purified 140 kd protein was subjected to SDS-PAGE under nonreducing conditions, a major band appeared at 120 kd (FIG. 2). In addition, a double band was seen at the position that is occupied by the single band under reducing conditions. No radioactivity was found in larger aggregates, indicating that the 140 kd protein is not cross-linked by disulfide bonds into oligomers. The increased mobility of the nonreduced protein in SDS-PAGE (120 kd vs. 140 kd) suggests that the molecule has a compact conformation stabilized by disulfide bonds. The conformation of the 140 kd protein is apparently influenced by intrachain disulfide bonds.

Figure 3:
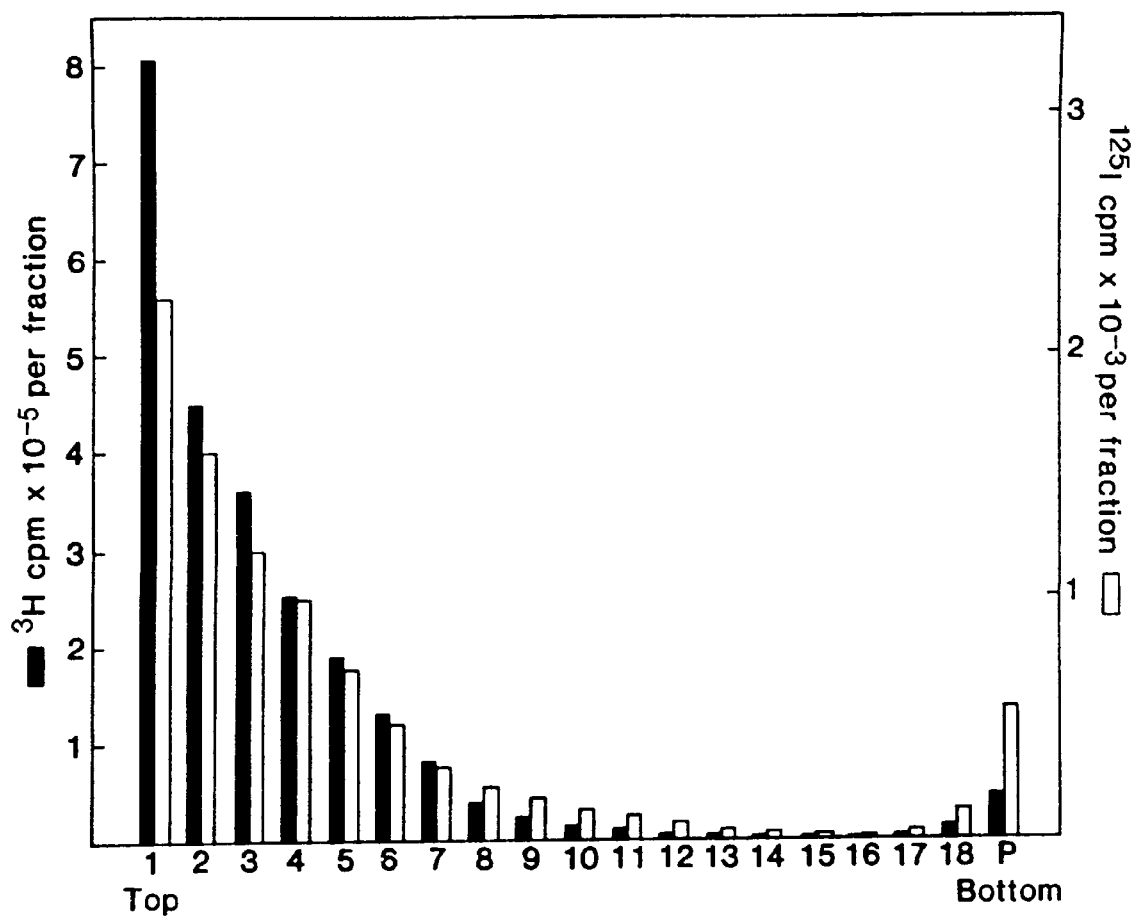
FIG. 3 is a graph depicting incorporation of the 140 kd protein into liposomes. A 140 kd protein fraction (0.5 ml) obtained by affinity chromatography as shown in FIG. 1 was supplemented with 200 µg of phosphatidylcholine and $2.5 \times 10^6$ cpm of $^3$H-phosphati-dylcholine and dialyzed against phosphate-buffered saline (PBS) containing 1 mM phenyl-methyl sulfonyl fluoride (PMSP) for 24 hr at 4° C. The resulting liposomes were fractionated by sucrose gradient centrifugation under conditions described herein. Two hundred microliter fractions of the gradient and the pellet (P) were analyzed for $^3$H-labeled lipid by liquid scintillation counting and for the $^{125}$I-labeled 140 kd protein by gamma counting. Note that interference by $^{125}$I in liquid scintillation counting was negligible, since the $^3$H radioactivity was present in a large excess relative to $^{125}$I.
Figure 4:
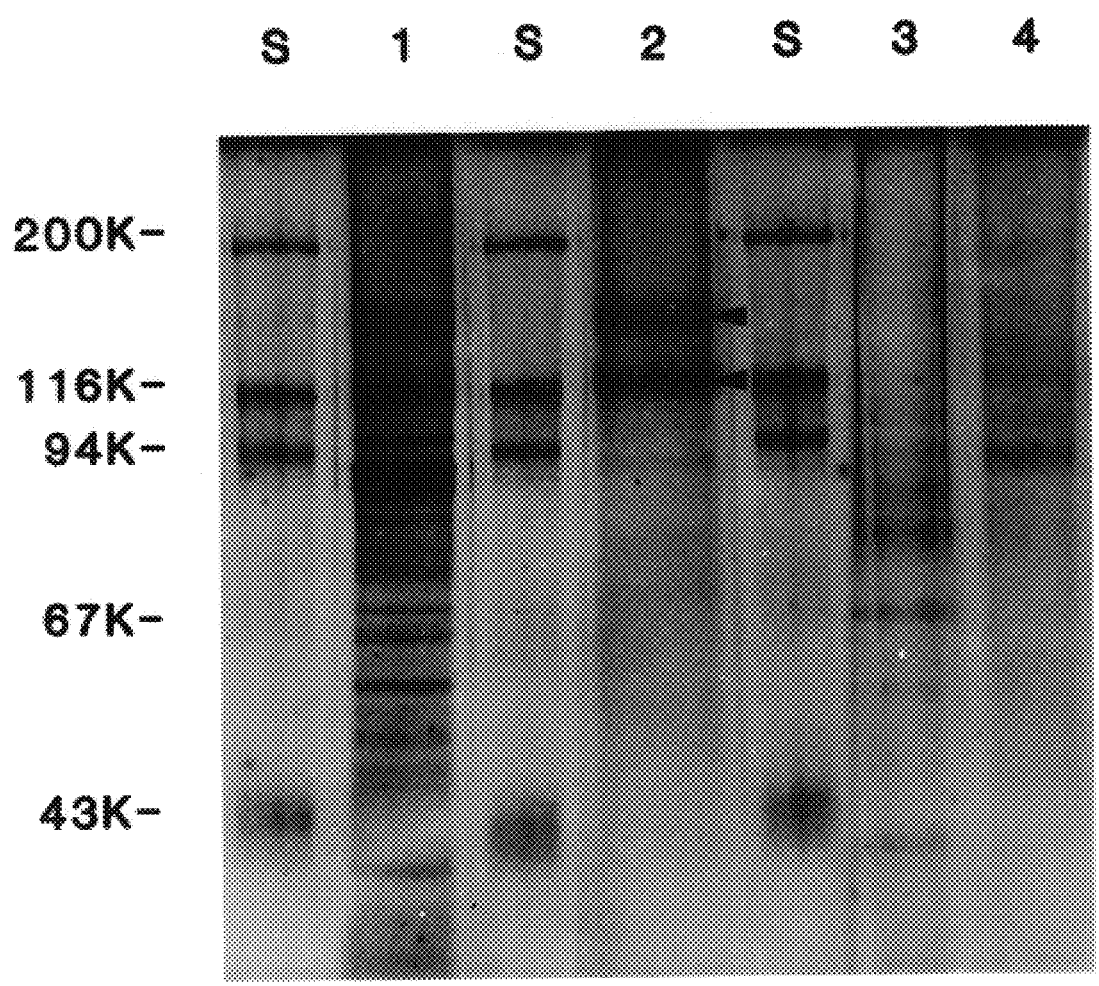
FIG. 4 is a representation of SDS-PAGE of fractions obtained after sucrose gradient fractionation of 140 kd protein-containing liposomes. Top and bottom fractions and the pellet of the sucrose gradient fractionation shown in FIG. 3 were analyzed by SDS-PAGE under nonreducing conditions, using silver staining for the visualization of the bands. Lane 1, 140 kd protein-containing fraction before incorporation into liposomes; lane 2, top fraction (liposomes); lane 3, bottom fraction (nonincorporated proteins); lane 4, pellet. Equal volumes (100 µl) of sample were applied to each lane. Molecular weight standards were run in the lanes marked S. Arrowheads indicate the position of the bands corresponding to the nonreduced form of the 140 kd protein.

A preparation containing $^{125}$I-labeled 140 kd protein dissolved in octylglucoside (as shown in FIG. 1, lane 10) was mixed with phosphatidylcholine (containing a tracer of $^3$H-phosphatidylcholine), and the mixture was freed of detergent by dialysis against phosphate-buffered saline (PBS). After centrifugation through a sucrose gradient with the sample loaded at the bottom of the tube, the distributions of the resulting liposomes and of the $^{125}$I-labeled protein were determined. As shown in FIG. 3, approximately 90% of the $^{125}$I-labeled protein codistributed with the tritium-labeled lipid vesicles. SDS-PAGE analysis of the top and bottom fractions and the pellet obtained by the centrifugation (FIG. 4) showed that most of the contaminating proteins present in the sample remained at the bottom of the tube or were pelleted, while the 140 kd protein migrated to the top of the gradient, appearing highly enriched in the liposome fraction. When the sucrose gradient centrifugation was carried out with a sample prepared without added phospholipid, most of the 140 kd protein radioactivity was recovered in the pellet fraction and none of it floated to the top of the gradient. Even when the detergent was not removed by dialysis, all of the reactivity remained in the lower fractions of the gradient, but did not precipitate. This indicates that floating of the 140 kd protein occurs only in the presence of phospholipid vesicles and is not due to the presence of residual detergent bound to the protein. These results indicate that the 140 kd protein can become inserted into a lipid bilayer.

Figure 5:
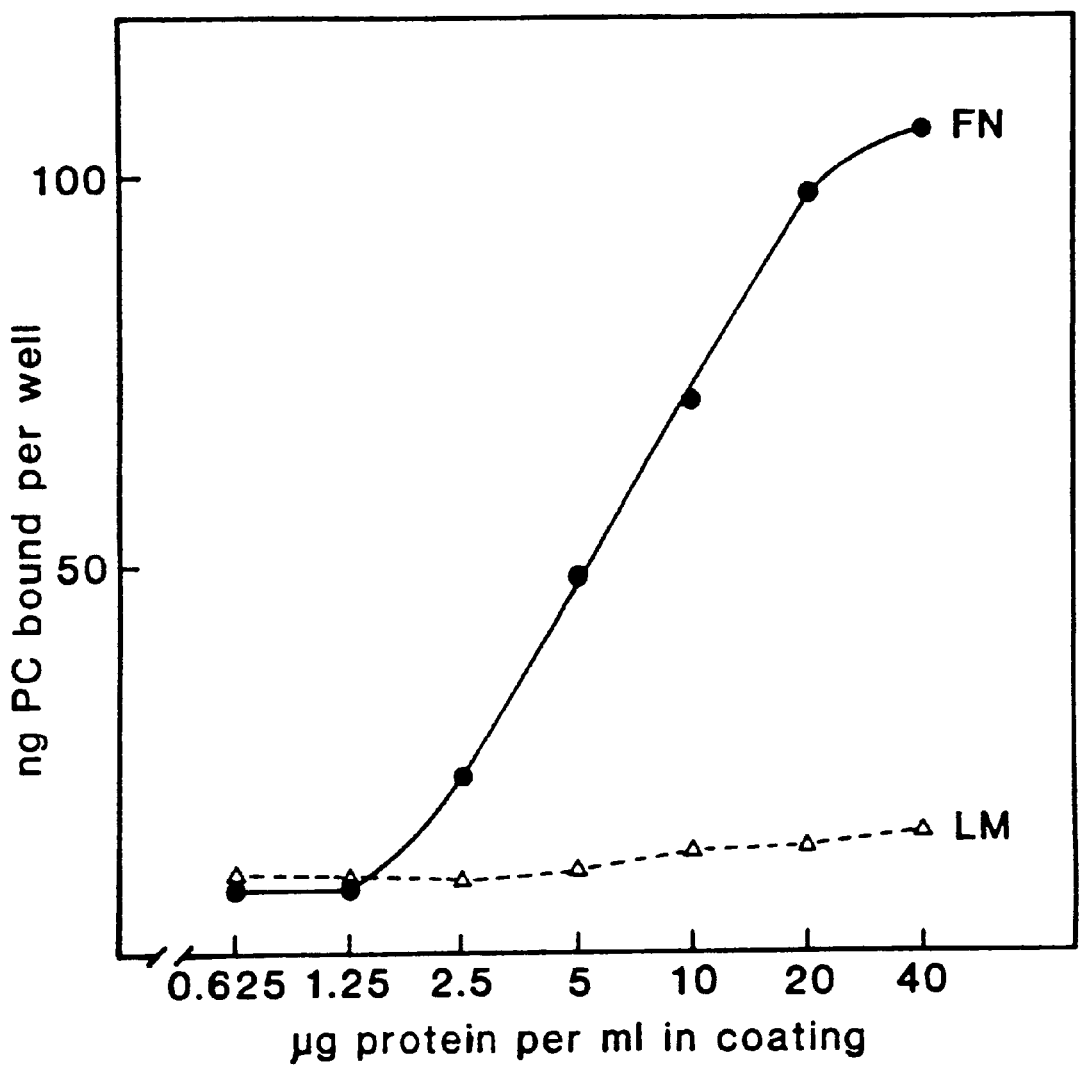
FIG. 5 is a graph depicting binding of the liposomes containing the 140 kd protein to fibronectin-coated substrate. $^3$H-labeled liposomes ($5 \times 10^4$ cpm/µg phosphatidylcholine) were prepared as described in the legend to FIG. 3. Fifty micrograms of phosphatidyl-choline (PC) and 140 kd protein from $2 \times 10^8$ cells (estimated to be approximately 10 µg based on staining in SDS-PAGE) were used. One hundred microliters of the liposome suspension (containing 3 µg phosphatidylcholine) were added to microtiter wells coated with various concentrations of fibronectin (FN) or laminin (LM), and the binding assay was carried out as described in Example I.
Figure 6:
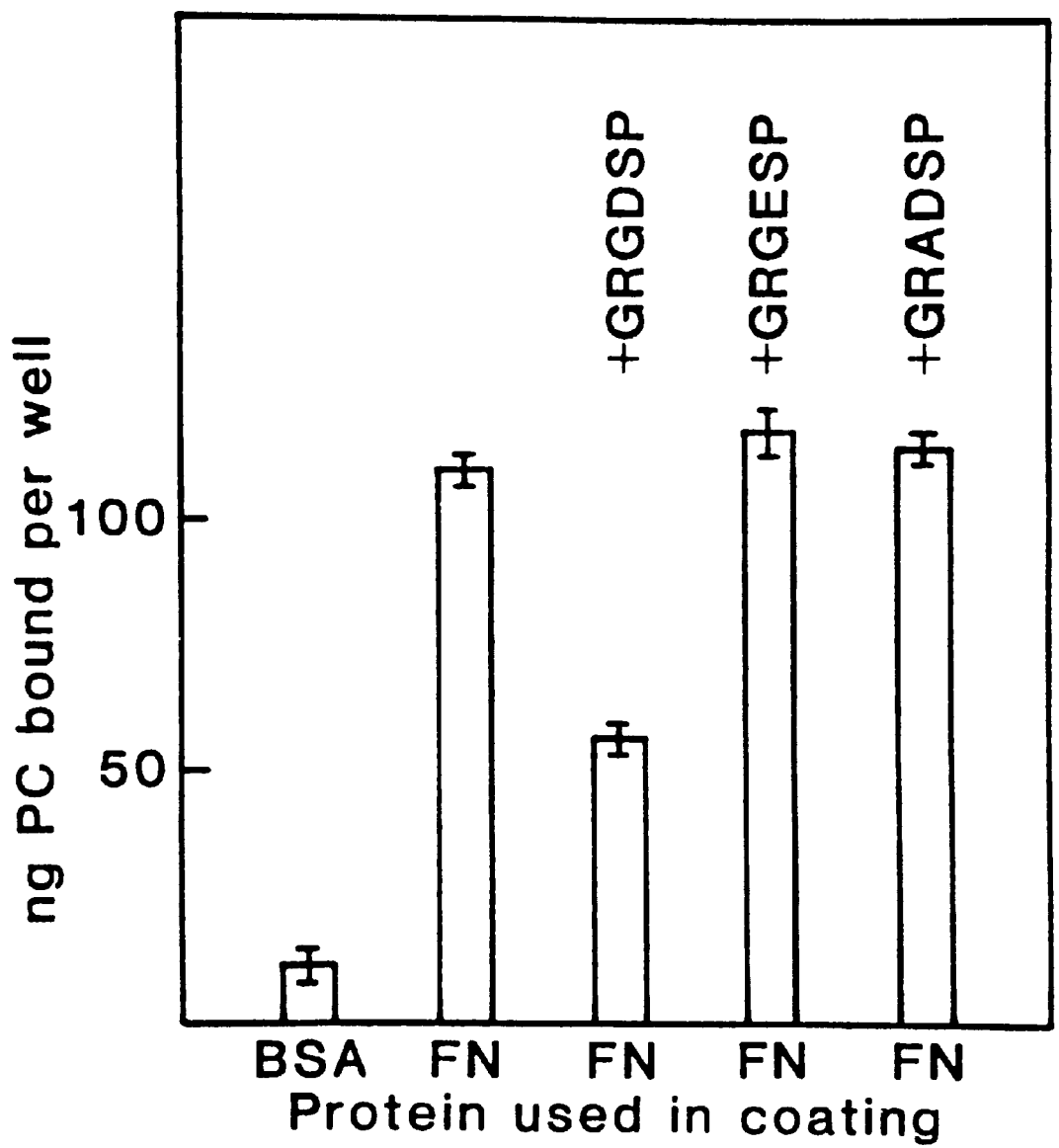
FIG. 6 is a graph depicting specificity of binding of the 140 kd protein-liposomes to fibronectin. The liposome-attachment assay was performed as in FIG. 5. The protein concentration used in the coating was 20 µg/ml. Where indicated, synthetic peptides (1 mg/ml) were added to the wells with the liposome suspension. The active cell-attachment peptide (GRGDSP) inhibits liposome binding by approximately 50%, while inactive variants have no effect. The mean and range are given for each condition.

As depicted in FIG. 5, liposomes containing the 140 kd protein bound to fibronectin-coated microtiter wells in a dose-dependent manner, similar to the attachment of cells to fibronectin. In contrast, no significant binding to another adhesive glycoprotein, laminin (Engvall, et al., 1983), was observed. In further control experiments, it was found that neither liposomes without incorporated protein nor liposomes prepared from a crude octylglucoside extract of cells adhered to fibronectin-coated wells. In addition, the binding was specifically inhibited by the cell-attachment peptide, GRGDSP (FIG. 6). This peptide, at a concentration of 1 mg/ml, inhibited the binding of liposomes by approximately 50%, while inactive variants, GRGESP and GRADSP (alanine replacing glycine in the latter peptide), were without any effect at the same concentration. Increasing the concentration of the peptides to 4 mg/ml resulted in a higher degree of inhibition, but at this concentration some apparent nonspecific inhibition was observed.

Figure 7:
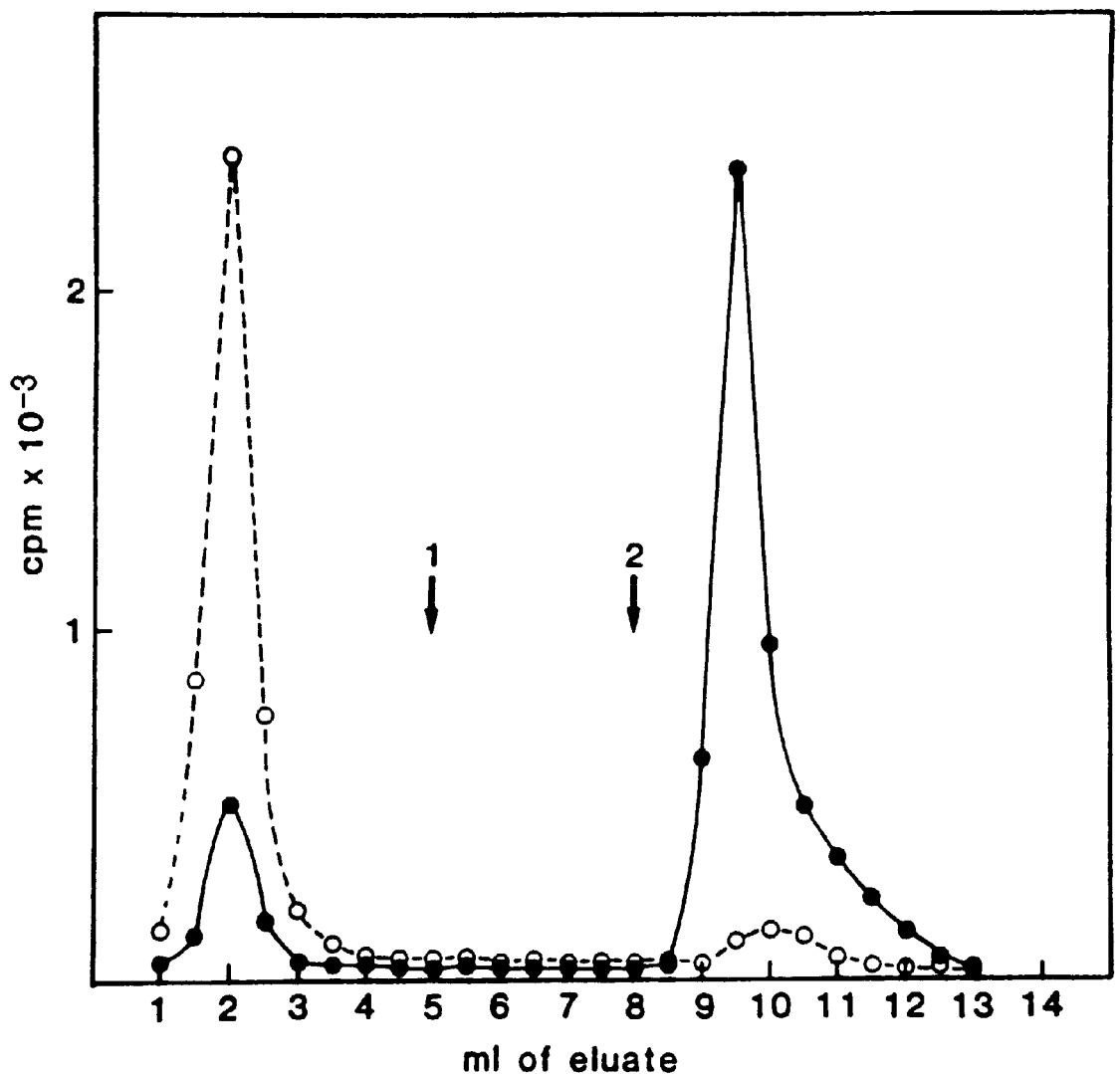
FIG. 7 is a graph depicting lectin affinity chromatography of 140 kd protein. $^{125}$I-labeled 140 kd protein obtained by fibronectin fragment chromatography was chromatographed on columns (bed volume, 1 ml) containing Wheat Germ-Agglutinin (WGA)-Sepharose or Concanavalin (Con) A-Sepharose. The columns were eluted with PBS containing 0.5 Nonidet-P40 and 1 mM PMSF, and supplemented with the appropriate sugar where indicated by arrows. Arrow 1 denotes the addition of α-methylmannoside (αMM) to the WGA-column and N-acetyl glucosamine (NAGA) to the ConA-column, arrow 2 shows the addition of NAGA to the WGA and . KMM to the ConA column.
Figures 8A, 8B:
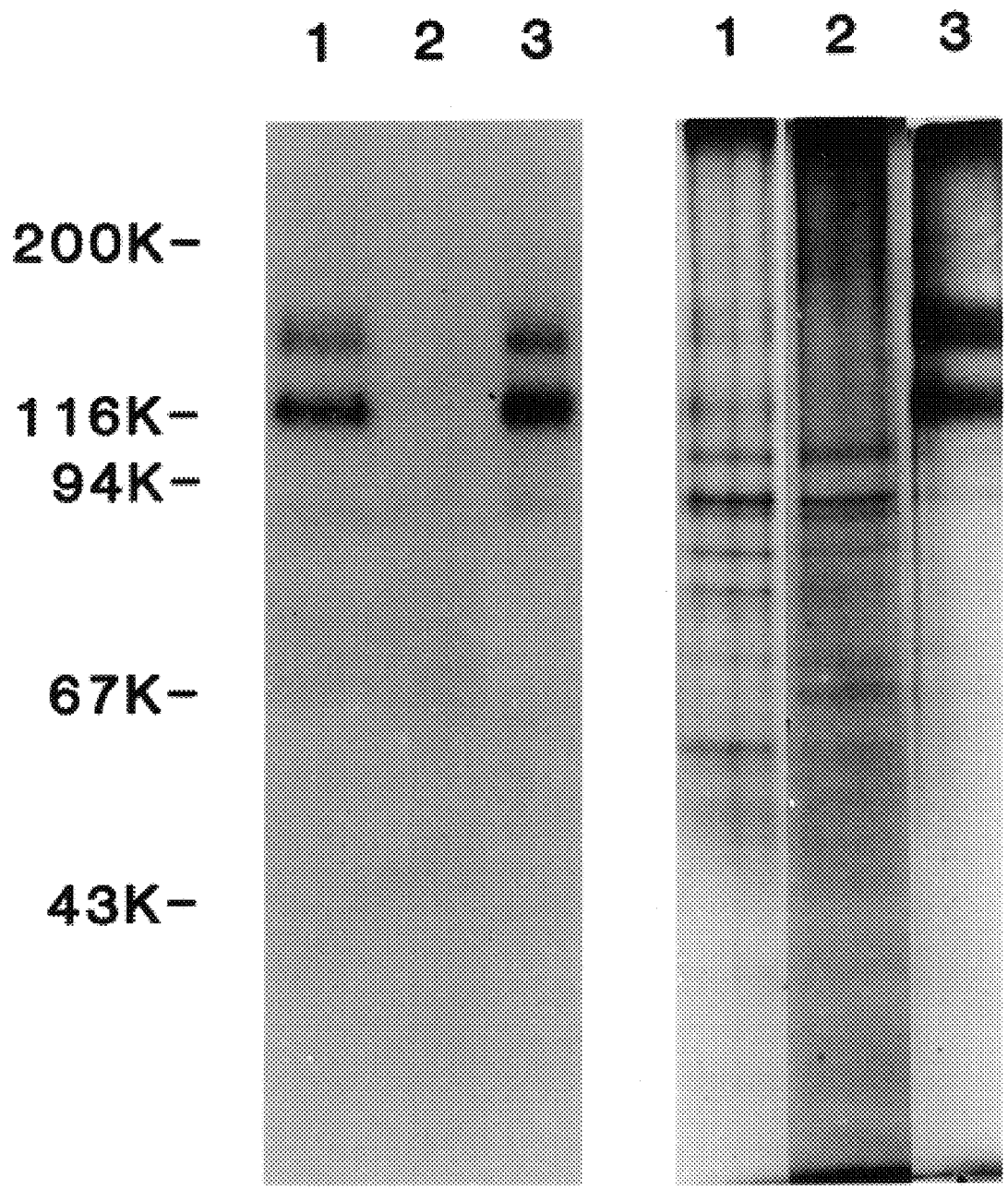
FIG. 8 is a representation of SDS-PAGE of the 140 kd protein eluted from WGA-Sepharose. The fractions obtained as shown in FIG. 7 were analyzed under nonreducing conditions using autoradiography (A) or silver staining (B) for the visualization of the protein bands. Lane 1, sample before application to the column; lane 2, material eluting in the flow-through; and lane 3, material eluted specifically by N-acetyl-glucosamine.

Chromatography on WGA-SEPHAROSE or ConA-SEPHAROSE of a fraction containing affinity-purified, radiolabeled 140 kd protein showed that most of the radioactivity binds to WGA and elutes specifically with N-acetylglucosamine, whereas it does not bind to Con A (FIG. 7). Analysis of the fractions by SDS-PAGE under nonreducing conditions confirmed the presence of the radiolabeled 140 kd protein in the fraction eluted with N-acetylglucosamine (FIG. 8A). Silver staining of SDS-PAGE showed that the WGA-bound material was further enriched for the 120 kd and 140 kd components characteristic of the nonreduced 140 kd protein (FIG. 8B, lane 3) relative to the preparation obtained from fibronectin fragment-SEPHAROSE (FIG. 8B, lane 1).

EXAMPLE I

Synthetic peptides were prepared by Peninsula Laboratories (San Carlos, Calif.) according to our specifications (Pierschbacher, et al., 1983; Pierschbacher and Ruoslahti, 1984a, 1984b). Fibronectin was prepared from human plasma according to Engvall and Ruoslahti (1977). Laminin was prepared from rat yolk sac tumor according to Engvall, et al. (1983). Egg yolk phosphatidylcholine was purchased from Sigma (St. Louis,Mo.), octylglucoside from Behring Diagnostics (La Jolla, Calif.). $^{125}$I-sodium iodide was from Amersham (Arlington Heights, Ill.) and $^3$H-phosphatidylcholine from New England Nuclear (Boston, Mass.). Chemicals used for SDS-PAGE were from BioRad (Richmond, Calif.).

MG-63 human osteosarcoma cells (Billiau, et al., 1977) were grown on 175 cm$^2$ tissue culture dishes in Dulbecco's Minimum Essential Medium (DMEM) supplemented with 5% fetal calf serum, glutamine, and penicillin/streptomycin. For subculturing or harvesting, confluent layers of cells were incubated in 1 mM Ethylenediamine Tetraacetic Acid (EDTA) for 15 minutes.

Cells grown to confluence in 175 cm$^2$ dishes were detached with 1 mM EDTA for 15 minutes, collected by centrifugation and resuspended in phosphate-buffered saline (PBS, 150 mM NaCl, 10 mM sodium phosphate, 1 mM CaCl$_2$, 1 MM MgCl$_2$, pH 7.3) containing 0.2 mM phenylmethyl sulfonylfluoride (PMSF; added from a 100× stock solution in ethanol). The suspended cells were radioiodinated according to Lebien, et al. (1982) using 2 mCi of $^{125}$I-sodium iodide and 0.2 mg/ml of lactoperoxidase per 10$^8$ cells. All subsequent operations were performed at 4° C. Cells were lysed by adding 1 ml of PBS containing 200 mM octylglucoside and 3 mM PMSF to 10$^8$ packed cells and incubating for 10 min. Insoluble material was removed by centrifugation at 12,500×g for 15 minutes.

The 120 kd chymotryptic cell binding fragment of fibronectin was prepared and coupled to cyanogen-bromide-activated SEPHAROSE (Sigma) as described (Ruoslahti, et al., 1981a; Pierschbacher, et al., 1981). This matrix contained 3 mg/ml of the chymotryptic fragment of fibronectin.

The octylglucoside extract of cells was then applied to 2 ml of this affinity matrix, which had been equilibrated in column buffer (PBS containing 50 mM octylglucoside and 1 mM PMSF). Elution with the synthetic cell-attachment peptide was carried out by slowly washing the column with 1 volumn column buffer supplemented with 1 mg/ml of GRGDSP over a period of 1 hour.

Samples of SDS-PAGE were boiled for 3 min in the presence of 3% SDS, with or without 5%

2-mercaptoethanol, and electrophoresed on 7.5% acrylamide gels according to Laemmli (1970). Molecular weight markers were myosin (200 kd), β-galactosidase (116 kd), phosphorylase B (94 kd), bovine serum albumin (67 kd), and ovalbumin (43 kd). Gels were silver-stained using a commercially available reagent kit (Bio-Rad), following the manufacturer's instructions. Autoradiography was performed by placing Kodak XAR X-ray film between the dried gel and a CRONER LIGHTNING PLUS intensifying screen (DuPont, Newtown, CT) at −70° C. for 1–3 days.

Liposomes were prepared essentially as described by Mimms, et al. (1981). Egg yolk phosphatidyl-choline was dried onto a glass tube under a stream of $N_2$ and dissolved in PBS containing 50 mM octylglucoside or protein fractions in this buffer. Detergent was removed by dialysis against PBS for 24 hours at 4° C., resulting in the formation of liposomes with an average diameter of approximately 200 nm, as judged by electron microscopy. To purify the liposomes, the suspension was made 45% in sucrose, overlaid with 2 ml of 30% sucrose and 1 ml of 10% sucrose, and centrifuged at 4° C. for 18 hours at 45,000 rpm in a Beckman SW60 rotor. The liposomes were recovered as a white band at the top of the 10% sucrose layer.

Wells of a polystyrene microtiter plate (Linbro/Titertek, Inglewood, Calif.) were coated with protein solutions in PBS by incubating overnight at room temperature. Unoccupied binding sites on the polystyrene surface were then saturated by incubation with 2 mg/ml bovine serum albumin (BSA) in PBS for 2 hours at 37° C. $^3$H-labeled liposomes suspended in PBS containing 2 mg/ml BSA were added to the wells and incubated for 5 hours at 4°C. The supernatants were then removed and wells were washed twice with PBS. Bound liposomes were dissolved in 1% SDS (100 µl/well) and quantitiated by scintillation counting.

INDUSTRIAL APPLICATION

This invention finds direct and immediate application in the assay of fibronectin receptor in cells and tissues. The isolation method described above can be used to assay cultured cells or tissue samples for their content of the fibronectin receptor. Such analysis will be important in determining the adhesion capacity of cells such as those in tumors. Alternatively, the isolated receptor can be used to prepare antibodies or such assays.

A reagent consisting essentially of the cell surface glycoprotein described in the foregoing examples may be used in therapy to carry reagents to selected tissues.

The cell surface glycoprotein is also useful in assaying for receptor antibodies and, together with such antibodies, will permit establishment of graft tissue assays for the receptor such as a radioimmunoassay or enzyme linked assay.

What is claimed is:

1. An antibody that specifically binds to a cell surface glycoprotein, wherein the glycoprotein:
   a. is a human cell surface glycoprotein;
   b. has an apparent molecular weight of about 140,000 Daltons when measured by SDS-polyacrylamide gel electrophoresis on a 7.5% gel under reducing conditions;
   c. has an apparent molecular weight of about 140,000 Daltons and 120,000 Daltons when measured by SDS-polyacrylamide gel electrophoresis on a 7.5% gel under non-reducing conditions; and
   d. specifically binds with the cell attachment site in fibronectin, and is elutable from the cell attachment site of fibrornectin by contacting with a peptide consisting essentially of the sequence GLY-ARG-GLY-ASP-SER-PRO.

* * * * *

UNITED STATES PATENT AND TRADEMARK OFFICE
CERTIFICATE OF CORRECTION

PATENT NO. : 6,242,577 B1
DATED : June 5, 2001
INVENTOR(S) : Ruoslahti et al.

It is certified that error appears in the above-identified patent and that said Letters Patent is hereby corrected as shown below:

<u>Title page, Item [54] and Column 1, line 1,</u>
Title, please delete "USE", replace therefor with -- USE OF --.

<u>Title page,</u>
Item [75], Inventors, please delete "Eric", replace therefor with -- Erkki --.

Signed and Sealed this

Twentieth Day of July, 2004

JON W. DUDAS
*Acting Director of the United States Patent and Trademark Office*